United States Patent [19]

Gross

[11] 4,310,593

[45] Jan. 12, 1982

[54] ABSORBENT ARTICLES CURED WITH AMINE-EPIHALOHYDRIN ADDUCTS

[75] Inventor: James R. Gross, Lake Jackson, Tex.

[73] Assignee: The Dow Chemical Company, Midland, Mich.

[21] Appl. No.: 219,072

[22] Filed: Dec. 22, 1980

Related U.S. Application Data

[63] Continuation-in-part of Ser. No. 796,627, May 13, 1977, abandoned.

[51] Int. Cl.$^3$ .................. B32B 27/00; D02G 3/00; B32B 27/00; A01N 1/02
[52] U.S. Cl. .................. 428/290; 128/156; 260/29.2 EP; 260/29.6 NR; 260/33.4 EP; 264/41; 264/49; 264/184; 264/203; 264/204; 264/331.18; 264/344; 427/2; 427/289; 427/389.9; 427/393.5; 428/245; 428/260; 428/364; 428/402; 428/500; 526/317
[58] Field of Search .............. 260/29.6 NR, 29.2 EP, 260/33.4 EP; 128/156; 428/364, 402, 500, 290, 245, 260; 427/289, 2, 389.9, 393.5; 264/204, 331, 344, 41, 49, 184, 203; 526/317

[56] References Cited

U.S. PATENT DOCUMENTS

| | | |
|---|---|---|
| 2,988,539 | 6/1961 | Cohen et al. . |
| 3,224,986 | 12/1965 | Butler et al. . |
| 3,393,108 | 7/1968 | Johnson . |
| 3,514,419 | 5/1970 | Darlow et al. . |
| 3,557,067 | 1/1971 | Bums et al. . |
| 3,669,103 | 6/1972 | Harper et al. . |
| 3,670,731 | 6/1972 | Harmon . |
| 3,926,891 | 12/1975 | Gross et al. . |
| 3,980,663 | 9/1976 | Gross . |
| 4,071,650 | 2/1978 | Gross ........................ 427/389.9 |
| 4,076,673 | 2/1978 | Burkholder . |

*Primary Examiner*—Michael R. Lusignan
*Assistant Examiner*—Janyce A. Bell
*Attorney, Agent, or Firm*—B. G. Colley

[57] ABSTRACT

Water absorbent articles, made from solutions of carboxylic polyelectrolytes, together with methods for their preparation, and a composition useful to make said articles are disclosed. The articles are cured and/or crosslinked with monomeric amine-epihalohydrin adducts by heating and/or removing substantially all of the solvent from the precursor composition.

The absorbent articles are useful as surgical sponges, diapers, tampons, meat trays, bath mats and the like.

27 Claims, No Drawings

ABSORBENT ARTICLES CURED WITH AMINE-EPIHALOHYDRIN ADDUCTS

CROSS REFERENCE TO RELATED APPLICATIONS

This application is a continuation-in-part of Ser. No. 796,627, filed May 13, 1977 and now abandoned.

BACKGROUND OF THE INVENTION

This invention relates to water absorbent articles made from crosslinked polyelectrolytes, methods for their preparation, and to a composition containing polyelectrolytes and monomeric amine/epihalohydrin adducts which is useful to make absorbent articles.

It is known from U.S. Pat. Nos. 3,669,103 and 3,670,731 that crosslinked polymeric sorbents can be sandwiched between flexible supports to achieve disposable diapers or dressings.

It is further known from U.S. Pat. Nos. 2,988,539; 3,393,168; 3,514,419, and 3,557,067 that water swellable crosslinked carboxylic copolymers can be prepared. However, these prior art copolymers are all crosslinked during copolymerization or crosslinked after polymerization with subsequent neutralization of the carboxylic acid groups to form water absorbent polyelectrolytes and hence these prior art polyelectrolytes cannot be crosslinked in-situ as an absorbent coating on a substrate or as a flexible film thereof.

The use of epihalohydrins to cure polyelectrolytes is disclosed in U.S. Pat. No. 3,980,663. However, these crosslinkers are inefficient, requiring up to 10% by weight of the epihalohydrins to obtain a suitable product.

The patent by N. D. Burkholder, U.S. Pat. No. 4,076,673 dated Feb. 28, 1978, discloses methods of curing polyelectrolytes to water absorbent articles wherein the curing or crosslinking agent is a polyamidepolyamine epichlorohydrin adduct such as Polycup ® 172 made by Hercules, Incorporated.

SUMMARY OF THE INVENTION

It now has been discovered that monomeric amine-epihalohydrin adducts can be used to cure or crosslink polyelectrolytes with greater efficiency, i.e., smaller amounts of the curing agent is needed than in the aforementioned application by Burkholder.

The present invention comprises a composition which is useful to form water absorbent articles of a carboxylic type synthetic polyelectrolyte which consists of lower alcohols, water, or mixtures thereof; about 10 to about 60 percent, preferably from about 15 to about 40 percent by weight based on the solvent of a carboxylic polyelectrolyte; and an amount of a water soluble amine/epichlorohydrin adduct sufficient to cure the polyelectrolyte into a water absorbent article.

A further advantage of the present invention is that the curing agents have greater thermal stability or longer shelf life compared to the known polyamidepolyamine epihalohydrin adducts which are polymeric products which crosslink with heat and/or ageing.

Another advantage of this invention is that the curing agent is monomeric and thus can be prepared, used, and shipped as a concentrate having a relatively low viscosity compared to the known polyamide-polyamine epihalohydrin adducts.

The invention further comprises methods of making discrete films, absorbent articles, particulates, fibers, and the products of these processes wherein the above composition on various substrates, is dried to crosslink the polyelectrolyte. The use of elevated temperatures is advantageous to accelerate the cross-linking and drying of the polyelectrolyte. However, if desired, the use of heat can be eliminated.

In order to obtain very high production rates of absorbent articles, it may be desirable to replace part or nearly all of the water in the polyelectrolyte solution with a lower alcohol such as methanol or ethanol. This substitution results in lower solution viscosities at a given percent solids and promotes rapid drying.

The final products of the present invention are thus water absorptive and are useful where ever diverse aqueous media such as urine, milk, blood, fruit juice, etc., need to be absorbed. Examples of the diverse utilities are surgical sponges, catamenial tampons, diapers, meat trays, paper towels, disposable door mats, disposable bath mats, and disposable litter mats for household pets.

DETAILED DESCRIPTION

Examples of carboxylic synthetic polyelectrolytes useful in this invention are the ammonium or alkali metal salts of homopolymers of acrylic or methacrylic acid and copolymers with one or more ethylenically unsaturated comonomers. The only limitation being that any copolymer to be useful in preparing highly absorbent polymers according to this invention, must be essentially water soluble in the salt form. The alternating copolymers of maleic anhydride and the maleic and fumaric acids and esters are useful when rendered water soluble by an appropriate base. One skilled in the art of radical addition copolymerization could prepare any number of suitable heteropolymers containing sufficient carboxylate functionality to render them water soluble and thus be useful in this invention.

A list of applicable carboxylic polymers which could be prepared from readily available monomers and converted into their salt form is as follows:

acrylic acid—acrylate copolymers
acrylic acid—acrylamide copolymers
acrylic acid—olefin copolymers
polyacrylic acid
acrylic acid—vinyl aromatic copolymers
acrylic acid—styrene sulfonic acid copolymers
acrylic acid—vinyl ether copolymers
acrylic acid—vinyl acetate copolymers
acrylic acid—vinyl alcohol copolymers
copolymers of methacrylic acid with all the above comonomers,
copolymers of maleic acid, fumaric acid and their esters with all the above comonomers,
copolymers of maleic anhydride with all the above comonomers.

If desired, the foregoing polyelectrolytes can also be sulfonated by treatment with $SO_3$, chlorosulfonic acid or fuming sulfuric acid in an inert organic solvent.

The monomeric amino-epihalohydrin adducts used in this invention are prepared by reacting at least two moles of an epihalohydrin with one mole of various primary and secondary monoamines, diamines and triamines at a temperature in the range from 0° to 90° C. for a time period of 0.5 to 8 hours. The amines used herein must have at least two free hydrogen atoms available for the substitution reaction. The reaction is carried out in a reaction media containing 20 to 90 percent water, lower alcohols such as methanol or ethanol, or in aqueous solutions of the lower alcohols. The amine-epihalohydrin adducts are used directly as made without separation or concentration.

The amino-epihalohydrin adducts used herein are known to have a plurality of 3-halo-2-hydroxy-propyl and azetidinium groups as is shown by Ross, et al, *J. Organic Chemistry* 29:824-6 (1964).

Examples of useful monoamines are ammonia, ethyl amine, methyl amine, and propyl amine.

Examples of useful diamines are bis-2-aminoethyl ether, N,N-dimethyl ethylene diamine, piperazine, and ethylenediamine.

Examples of useful triamines are N-aminoethyl piperazine, and dialkylene triamines such as diethylene triamine, and dipropylene triamine.

The epihalohydrins used herein can be epichlorohydrin, epibromohydrin and epiiodohydrin. Epichlorohydrin is preferred because of its lower cost and availability.

In the preferred method of making water absorbent films by the present invention, the above composition of the polyelectrolytes is spread on a flat plate or roller of metal, plastic or other impervious substrate and dried to crosslink the polyelectrolyte and drive off the excess water and/or alcohol. The film is then peeled off the plate or roller by a scraper to recover the intact film for subsequent storage or use.

It is sometimes desirable to add a small amount of a surfactant to the polyelectrolyte composition to aid in flowing on and removing the continuous film from the water impervious substrate. A secondary benefit of using a surfactant is to increase the wettability of the final dry absorbent film. Either anionic or nonionic surfactants may be used. Examples of the useful surfactants are the sodium alkyl sulfonates and the ethylene oxide derivatives of alkylated phenols and the like.

Similarly, when an absorbent article is prepared, the article which is to be the substrate is coated with the composition of the polyelectrolyte and then the coating is crosslinked. It is to be understood that for the purposes of this invention the coating step implies a complete coating or a discontinuous coating, thus when a fibrous substrate such as cellulose batting, paper, woven or non-woven cloth, polyurethane foam and the like are used as the substrate, the composition can be applied in a discontinuous manner, i.e., in a pattern of large dots, squares, or grid lines to retain the inherent flexibility of the fibrous substrate and at the same time vastly improve its water absorbency. Wood pulp can be coated by slurrying it in the polyelectrolyte composition followed by a fluffing operation.

If desired, the water swellable film prepared as above can be used per se as the inner absorbent layer in baby diapers. It is sometimes advantageous that the film be disintegrated into flakes, strips or powders. This is accomplished by crushing or comminuting the film in a hammer mill, blenders or the like. If long flat strips are desired, the film can be sliced widthwise with appropriate slicers.

In some instances, water swellable fibers are desired. These can be prepared by extruding the above composition of the polyelectrolytes into a bath comprising lower alkyl ketones such as acetone, methyl ethyl ketone, diethyl ketone and the like. Alcoholic compositions may be extruded into a non-aqueous coagulant such as chlorinated hydrocarbons, i.e., methylene chloride, perchloroethylene and the like. The soft extruded fibers are then removed from the bath by any convenient means such as a three or five roll cluster and carried through a heated chamber at a temperature greater than about 30° C. and preferably in the range from about 70° C. to about 150° C. to dry and to crosslink the polyelectrolyte fibers.

The absorbency of the crosslinked polyelectrolytes (grams solution gelled per gram of polyelectrolyte) is determined in the following manner using synthetic urine (0.27 N sodium chloride solution).

A 0.5 gram sample of a crosslinked polyelectrolyte is weighed into a 250 ml. beaker, a 0.27 N sodium chloride solution (150 ml) is poured into the beaker and allowed to soak for 15 minutes at room temperature, with occasional stirring. The swelled polyelectrolyte is then collected by filtration and the gel capacity is reported as grams of solution gelled per gram of polymer salt.

For the purposes of the invention, a moisture or water absorbent polyelectrolyte is defined as one which absorbs greater than about 20 times its weight of synthetic or natural urine. Preferably, the absorbency should be in the range from about 30–60 grams of urine per grm of resin or polyelectrolyte. The level of crosslinking agent used is a variable factor which is dependent upon the particular polyelectrolyte used and the molecular weight of the polyelectrolyte. In general, the amount used varies from 0.1 to 2.0 percent based on the weight of the polyelectrolyte. However, this range is varied for each polyelectrolyte in order to adjust the absorbency of the final crosslinked gel so that it is at least 20 and preferably in the range from about 30 to about 60 grams of urine per gram of resin.

PREPARATION OF EPIHALOHYDRIN-AMINE ADDUCTS - TABLE I

On a mole basis, one mole of the amines was reacted with two moles of the epihalohydrins listed in Table I in various solvents and concentrations. The reactions were carried out at 65° C. for 60 minutes in a hot water bath in sealed 2-ounce bottles. The epiamine adducts were used directly from the bottles as curing agents.

TABLE I

| | CURING AGENTS | | | |
|---|---|---|---|---|
| Preparation | Amine | ECH* or EBH (g) | Solvent (g) | % Solids or Non-Volatiles |
| 1 | 1.9 g piperazine hydrate | 1.8,ECH | 16.3 H₂O | 12.5% |
| 2 | 1.9 g piperazine hydrate | 1.8,ECH | 16.3 methanol | 12.5 |
| 3 | 1.9 g piperazine hydrate | 1.8,ECH | 7.5 H₂O | 25.0% |
| 4 | 1.9 g piperazine hydrate | 1.8,ECH | 1.4 methanol | 50.0% |
| 5 | 1.9 g piperazine hydrate | 2.74,EBH | 19.3 methanol | 15.0% |
| 6 | 1.3 g N-aminoethyl piperazine | 1.8,ECH | 17.7 methanol | 15.0% |
| 7 | 0.6 g ethylenediamine | 1.8,ECH | 13.6 methanol | 15.0% |
| 8 | 1.0 g Bis(2-aminoethyl)-ether | 1.8,ECH | 16.1 methanol | 15.0% |
| 9 | 1.0 g diethylenetriamine | 1.8,ECH | 16.1 methanol | 15.0% |
| 10 | 0.64 g ethylamine | 1.8,ECH | 12.5 methanol | 15.0% |
| 11 | 0.88 g N,N-dimethylethylenediamine | 1.8,ECH | 15.2 methanol | 15.0% |
| 12 | 0.68 ml conc. | 1.8,ECH | 10.8 | 15.0% |

TABLE I-continued

| | CURING AGENTS | | |
|---|---|---|---|
| Preparation | Amine | ECH* or EBH (g) | Solvent (g) | % Solids or Non-Volatiles |
| | NH$_4$OH | | methanol | |

*ECH—epichlorohydrin
EBH—epibromohydrin

EXAMPLES 1-9

Three mixtures were made up having the following compositions:

| Part A | Part B | Part C |
|---|---|---|
| 600 g deionized water | 437.5 g ethyl acrylate | 175 g deionized water |
| 0.75 g Triton GR-5* | 77.2 g methacrylic acid | 2.0 g sodium bisulfite |
| 1.75 g sodium persulfate | | |

*dioctylsodium sulfosuccinate

Part A was charged to a 2-liter reactor and brought to 40° C. while under vigorous nitrogen purge. Eighteen milliliters of Part B was added to the reactor followed by all of Part C. The remainder of Part B was added over the next 2.5 hours while the temperature was held at 39°-41° C. The latex was then digested at 60° C. for 1.5 hours, cooled to 30° C. and bottled. The latex contained 40.6% non-volatiles.

1125 g of the above latex was added in a small stream over a period of 25 minutes to a slowly stirred solution of 187.16 g 50% NaOH in 547.9 g deionized water. After the polymer had all dissolved, the viscous solution was heated at 50° C. for 22 hours to complete the spaonification. The resulting solution (25.4% solids) had a Brookfield viscosity of 16,200 cps at 25° C. (No. 5 spindle, 10 rpm). The polymer is 50% ethylacrylate by moles with the remainder being 22% sodium acrylate and 28% methacrylate.

Samples of the above solution were blended with various curing agents at a level of 0.5% solids basis, as set forth in Table II hereinafter and cast on polished chromium plate with a 25 mil draw bar. After air drying, the films were lifted from the plate and placed in a 150° C. oven for 30 minutes. The absorbency (gel capacity) of the various films in 0.27 N NaCl was determined by the method set forth above. The gel strength index was determined by the method set forth in Ser. No. 593,413 filed July 7, 1975, now abandoned. This disclosure is incorporated by reference herein.

The index in pounds per square inch (psi) is an assessment of the thoroughness of the cure. The best moisture absorbent polymer will possess both a high absorbency and a high gel strength. In general, this means about 20 to 60 absorbency in grams gel per gram of film and about 0.5 to 2.0 gel strength index in pounds per square inch.

Although most of the amine-epihalohydrin adducts shown in Table II lost curing effectiveness after aging overnight at 65° C., the previously known curing agent, Polycup ® 172, could not even be evaluated as it had self-crosslinked. Three of the amine adducts (Examples 6, 7, and 8) actually increased in curing effectiveness upon accelerated aging, indicating that they were not completely reacted when first prepared.

Curing effectiveness or the degree or extent of crosslinking is indicated by the absorbency and gel strength at a given level of crosslinker. A more effective crosslinker will produce a lower absorbency and correspondingly higher gel strength. For example, in Example 8 the absorbency decreases from 36.5 to 24.9 after an accelerated aging time while the gel strength increased from 1.0 to greater than 2.1.

TABLE II

Example 1-8

| | | Properties of Film Made With | |
|---|---|---|---|
| | Curing Agent From Table I | Fresh Curing Agent Absorbency/ Gel Strength | Old Curing Agent* Absorbency/ Gel Strength |
| Control A | Polycup ® 172 | 43.7/0.43 | curing agent gelled |
| Example 1 | 1 | 24.4/>2.2 | 29.6/1.5 |
| Example 2 | 6 | 35.3/1.5 | 33.5/1.75 |
| Example 3 | 7 | 41.4/1.1 | 44.0/0.63 |
| Example 4 | 8 | 32.2/2.0 | 41/1.0 |
| Example 5 | 9 | 55.5/0.49 | 53.5/0.25 |
| Example 6 | 10 | 24.1/>2.2 | 17.3/>2.1 |
| Example 7 | 11 | 75.5/<0.13 | 63.7/0.13 |
| Example 8 | 12 | 36.5/1.0 | 24.9/>2.1 |

*curing agent was held at 65° C. for 17 hours before use to simulate 6 months storage at 25° C.

EXAMPLES 9-11

The amount of curing agent used is varied to compare the absolute curing effectiveness of a typical amine-epihalohydrin adduct to a commercial polyamidepolyamine epihalohydrin adduct (Polycup ® 172).

The non-volatiles from a curing agent preparation like preparation 2 in Table I were used instead of the original solution. The films were heated at 150° C. for 15 hours to assure complete reaction of the curing agent. A low absorbency and high gel strength indicates a better cure.

TABLE III

| Example | Curing Agent | % Curing Agent | Absorbency/ Gel Strength |
|---|---|---|---|
| Control B | Polycup 172 | 0.5 | 41.5/0.6 |
| Control C | Polycup 172 | 0.25 | 55.5/0.19 |
| 9 | Prep. 2, Table I | 0.5 | 27/2.1 |
| 10 | Prep. 2, Table I | 0.25 | 31/1.25 |
| 11 | Prep. 2, Table I | 0.2 | 38.5/0.79 |

EXAMPLES 12-14

Films were prepared as before and cured at 150° C. for 60 minutes using the epibromohydrin-piperazine adduct of preparation 5, Table I. They had the following properties as a function of level of use in the polyelectrolyte.

TABLE IV

| Example | Curing Agent from Table I | % Curing Agent | Absorbency/ Gel Strength |
|---|---|---|---|
| 12 | 5 | 1.0 | 25.5/2.1 |
| 13 | 5 | 0.5 | 35.9/0.91 |
| 14 | 5 | 0.25 | 57.8/0.33 |

Due to the higher equivalent weight of the bromine compound, the cure efficiency on a weight basis is not as good as the epichlorohydrin adduct to piperazine but is still better than the polyamidepolyamine adduct.

EXAMPLES 15–16

To illustrate that these new curing agents can be prepared at high solids without loss of efficiency, films were prepared using 0.25% curing agent by weight polyelectrolyte and cured at 150° C. for 90 minutes then evaluated as usual.

TABLE V

| Example | Curing Agent from Table I | Absorbency/ Gel Strength |
| --- | --- | --- |
| 15 | 1 (12.5% solids) | 39/0.88 |
| 16 | 3 (25.0% solids) | 40/0.96 |

I claim:

1. A curable composition useful to form water absorbent articles of a carboxylic synthetic polyelectrolyte which comprises a solution of
   (1) a member selected from the group consisting of water, lower alcohols, and mixtures thereof,
   (2) about 10 to about 60% by weight based on the amount of (1) of a carboxylic polyelectrolyte or mixtures thereof, and
   (3) an amount of a monomeric water soluble amine/epihalohydrin adduct sufficient to cure said polyelectrolyte into a water absorbent article.
2. The composition of claim 1 wherein the monomeric water soluble adduct is the reaction product of two moles of an epihalohydrin with one mol of a mono, di, or tri amine having at least two free hydrogen atoms.
3. The composition of claim 2 wherein the reaction product is the reaction of two moles of an epihalohydrin with one mol of a monoamine.
4. The composition of claim 3 wherein the reaction product is the reacton of two moles of an epihalohydrin with one mol of a diamine.
5. The composition of claim 3 wherein the reaction product is the reaction of two moles of an epihalohydrin with one mol of a triamine.
6. The composition of claim 4 wherein the reaction product is the reaction of two moles of an epihalohydrin with one mol of a piperazine.
7. The composition of claims 1 or 2 wherein the amount of carboxylic polyelectrolyte is about 15 to about 40% by weight.
8. The composition of claims 1 or 2 wherein the carboxylic polyelectrolyte is an ammonium or alkali metal salt of the homopolymers of acrylic acid or methacrylic acid.
9. The composition of claim 8 wherein the amount of homopolymer is about 15 to about 40% by weight.
10. The composition of claims 1 or 2 wherein the carboxylic polyelectrolyte is an ammonium or alkali metal salt of the copolymers of acrylic or methacrylic acid with monoethylenically unsaturated monomers.
11. The composition of claim 10 wherein the amount of copolymer is about 15 to about 40% by weight.
12. The composition of claim 10 wherein the carboxylic polyelectrolyte consists of a terpolymer of ethyl acrylate, sodium acrylate, and sodium methacrylate with 50 mole percent being ethyl acrylate.
13. A method of preparing a water absorbent polyelectrolyte which comprises the steps of
    (1) preparing a composition as set forth in claims 1 or 2,
    (2) evaporating about 75% of the solvent therefrom to obtain a substantially dry water-absorbent polyelectrolyte.
14. A method of preparing a substantially dry, water-absorbent polyelectrolyte film which comprises the steps of
    (1) preparing a composition as set forth in claim 1 or 2,
    (2) spreading a coating of said composition on an impervious substrate,
    (3) drying said coated substrate to crosslink said polyelectrolyte, and
    (4) separating said crosslinked polyelectrolyte film from said substrate.
15. A method of preparing an absorbent article coated with a substantially dry water absorbent polyelectrolyte which comprises
    (1) preparing a composition as set forth in claim 1 or 2,
    (2) applying a coating of said composition on a relatively thin article,
    (3) drying said coated article to crosslink said polyelectrolyte.
16. The method of claim 15 wherein the article is a natural or a synthetic fibrous substrate.
17. The method of claim 15 wherein the article is a synthetic film.
18. The method of claim 15 wherein the article is a foamed polymer.
19. A method of preparing a substantially dry water-absorbent particulate polyelectrolyte which comprises
    (1) preparing a film as set forth in claim 10, and
    (2) disintegrating said film to form flakes, strips, or powders thereof.
20. A method of preparing substantially dry water absorbent polyelectrolyte fibers which comprises
    (1) preparing a composition as set forth in claim 1 or 2,
    (2) extruding said composition into a bath comprising lower alkyl ketones or chlorinated hydrocarbons to form an extruded fiber,
    (3) separating the extruded fibers from said bath, and
    (4) drying said fibers to crosslink said polyelectrolyte.
21. The film prepared by the method of claim 14.
22. The particulate polyelectrolyte produced by the method of claim 19.
23. The polyelectrolyte fiber produced by the method of claim 20.
24. The coated article produced by the method of claim 15.
25. The coated article produced by the method of claim 16.
26. The coated article produced by the method of claim 17.
27. The coated article produced by the method of claim 18.

* * * * *